United States Patent
Braun et al.

(10) Patent No.: US 6,861,451 B2
(45) Date of Patent: Mar. 1, 2005

(54) CARBOXYLIC ACID FLUORIDES AS PESTICIDES

(75) Inventors: Max Braun, Wedemark (DE); Francine Janssens, Vilvoorde (BE); Reiner Fischer, Dettum (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 0 days.

(21) Appl. No.: 10/116,125

(22) Filed: Apr. 5, 2002

(65) Prior Publication Data

US 2003/0017186 A1 Jan. 23, 2003

Related U.S. Application Data

(63) Continuation of application No. PCT/EP00/09544, filed on Sep. 29, 2000.

(30) Foreign Application Priority Data

Oct. 7, 1999 (DE) .......................... 199 48 496
Aug. 23, 2000 (DE) .......................... 100 41 425

(51) Int. Cl.$^7$ .................. A01N 29/00; A01N 29/02
(52) U.S. Cl. .................. 514/743; 514/744; 514/746
(58) Field of Search ................ 514/743, 744, 514/746

(56) References Cited

U.S. PATENT DOCUMENTS

| | | | | |
|---|---|---|---|---|
| 2,875,127 A | | 2/1959 | Kenaga et al. | |
| 3,069,395 A | * | 12/1962 | Middleton | .................. 528/390 |
| 3,679,720 A | * | 7/1972 | Siddall | ........................ 260/408 |
| 4,544,504 A | | 10/1985 | Prestwich | |
| 6,203,824 B1 | | 3/2001 | Banks et al. | |
| 6,521,018 B2 | * | 2/2003 | Hobbs et al. | ................. 75/585 |

FOREIGN PATENT DOCUMENTS

| | | | |
|---|---|---|---|
| JP | 61088833 | * | 5/1986 |
| WO | 93/13659 | | 7/1993 |
| WO | 00/32549 | | 6/2000 |

OTHER PUBLICATIONS

Fuoshin et al, Electrolysis of a solution of potassium difluorideNauchnye Doklady Vysshei Shkloy, Khimiyai Tekhologiya, 1958, no. 3, pp. 533–535.*

Kumar e al, Time–resoved infrared fluorescence from an IR multphoton dissociation product of trifluoroacetid anhyride, Chemical Physics Letters, 1992, 200 (3), 283–9.*

Kutsuna et al, Photocatalyic Degradation of Some Methyl Perfluoroalkyl Ethers on TiO2 Particles in Air, Environmenal Science and Technology, 1999, 33 (7), 1071–6.*

Nesmeyanov et al, Direct synthesis of acid fluorides from acids and the prepartation of formyl fluoride, Ber. (1934), vol. 67B, pp. 370–373.*

Morse Associates, "Pressure Differential Isolation of Airborne Contamination" (http://www.morse-associates.com/pressure.html).

* cited by examiner

*Primary Examiner*—Alton Pryor
(74) *Attorney, Agent, or Firm*—Crowell & Moring LLP

(57) ABSTRACT

Carboxylic acid fluorides having a boiling point of preferably less than 100° C. are suitable for use as pesticides. Acetyl fluoride is highly suitable, and Chlorodifluoroacetyl fluoride and trifluoroacetyl fluoride are also very useful. Mixtures of carboxylic acid fluoride pesticides and other pesticides are also disclosed.

15 Claims, No Drawings

CARBOXYLIC ACID FLUORIDES AS PESTICIDES

CROSS REFERENCE TO RELATED APPLICATIONS

This application is a continuation of international patent application no. PCT/EP00/09544, filed Sep. 29, 2000, designating the United States of America, the entire disclosure of which is incorporated herein by reference. Priority is claimed based on Federal Republic of Germany patent application Nos. DE 100 41 425.7, filed Aug. 23, 2000, and DE 199 48 496.1, filed Oct. 7, 1999.

BACKGROUND OF THE INVENTION

The invention relates to the use of carboxylic acid fluorides as pesticides. It is known in the art to use sulfuryl fluoride as a pesticide; see U.S. Pat. No. 2,875,127, for example. Pests or fungi can be controlled, for instance, in installed or uninstalled building timber, even in freshly cut timber. Buildings attacked by pests, such as beetles or termites, as well as storage areas can be disinfested. Also known is the disinfestation of museums, churches, or mills. It is also known to use sulfuryl fluoride in combination with carbon dioxide, inert gases, or other pesticides.

In accordance with the invention it has been found that carboxylic acid fluorides can be used as pesticides. The term "carboxylic acid fluorides" preferably encompasses carboxylic acid fluorides containing a total of 2 to 7 carbon atoms. Preferred are aliphatic carboxylic acid fluorides. Compounds with a saturated alkyl group are especially preferred. Also usable are carboxylic acid fluorides that have one or more carbon-carbon double or triple bonds. The alkyl, alkenyl or alkynyl group can also be substituted, e.g., by 1 or more halogen atoms, e.g., 1 or more fluorine atoms. Particularly useful are carboxylic acid fluorides with a total of 2 to 4 carbon atoms, especially those with saturated alkyl groups. They can be substituted by 1 or more halogen atoms, preferably chlorine and/or fluorine atoms. Particularly preferred carboxylic acid fluorides are fluorides corresponding to the formula RC(O)F, where R represents methyl, ethyl, difluoromethyl, trifluoromethyl and difluorochloromethyl. The boiling point of preferred carboxylic acid fluorides is preferably less than 45° C., especially less than 35° C.

If desired, the carboxylic acid fluoride can be used in combination with other pesticides (fumigants). Carboxylic acid fluoride can, for instance, be used together with inert gases (nitrogen, noble gases) and/or carbon dioxide. The inert gases and $CO_2$ can serve as auxiliary gases, for example as carrier gases, e.g., in compounds with a higher boiling point. Other fumigants can of course also serve as carrier gases. However, inert gases and $CO_2$ also have pesticidal properties. The carboxylic acid fluoride and the other fumigant(s) and/or $CO_2$ can be used premixed or separately, simultaneously or successively, or overlapping in time. Preferred pesticides used in addition also have a boiling point of less than 100° C. under normal conditions, preferably less than 45° C., particularly less than 35° C. Alternatively, an atomizing agent can be used. Carbon dioxide has the advantage that the carboxylic acid fluoride concentration can be reduced, since carbon dioxide increases the toxicity of the carboxylic acid fluorides (increased respiration rate of the pests).

It is, of course, also possible to take measures that are typically used in fumigation processes and are known per se. For instance, moisture can be reduced during fumigation, e.g., by introducing drying agents (e.g., $SiO_2$) or by guiding the treatment gas atmosphere continuously or discontinuously across a drying agent. Fumigation may be carried out in several steps. For initial fumigation, the conditions, particularly with respect to the fumigant concentration, are selected so that the larvae and the adults are destroyed. The second and possibly a third or additional fumigation steps are carried out if eggs that were not previously destroyed develop into larvae or adults. It is known that the fumigant concentration to combat larvae or adults can typically be lower than the concentration necessary to destroy eggs. If the concentration is selected such that only the larvae or the adults are destroyed but the process is repeated several times whenever new larvae or adults have developed, the use of fumigant can be reduced.

As an alternative, fumigation may also be carried out using fumigants that are known ovicides, e.g., in combination with hydrocyanic acid, formic acid esters, alkylisothiocyanates or $PH_3$. If desired, the fumigation process may also be carried out in combination with atomizing agents, such as pyrethroids, as described in published German patent application no. DE-OS 197 47 648. As disclosed in Austrian Patent 154,481, it is also possible to arrange a balloon in the room to be fumigated so as to reduce the room volume and thus to save fumigant.

In the method according to the invention, one or more carboxylic acid fluorides can be used as the only pesticide. It is also possible, however, to use carboxylic acid fluoride(s) in combination with other pesticides. For instance, carboxylic acid fluorides can be used together with one or more pesticides selected from the group consisting of sulfuryl fluoride, sulfuryl chlorofluoride, nitrogen, noble gases, carbon dioxide, carbonyl sulfide, $PH_3$, alkyl phosphines (mono-, di- and trialkyl phosphines), $SF_6$, inorganic and organic compounds with the CN group, organic esters, organic nitro compounds, halogenated hydrocarbons, alkynols, thiocyanate esters, isothiocyanate esters, chloropicrin, ethylene oxide, sulfonyl fluorides, and the aforementioned atomizing agents. The esters used are preferably alkyl esters, for instance, alkyl esters of formic acid, acetic acid, etc. Chloropicrin can be used as a warning agent.

The usefulness of carbonyl sulfide as a fumigant is disclosed in U.S. Pat. No. 6,203,824 (=WO 93/13659). Suitable formic acid esters are disclosed, for instance, in published German patent application no. DE-OS 197 47 640. Suitable acetic acid esters are described in published German patent application no. DE-OS 197 58 318. Suitable alkynols or thiocyanate esters are described in published German patent application no. DE-OS 198 01 332. Other carbonic acid esters are described also in published German patent application no. DE-OS 198 13 894. Useful nitro compounds are set forth in published German patent application no. DE-OS 198 04 508. Suitable sulfonyl fluorides are disclosed in German patent DE 196 33 595. Hydrocyanic acid and $CF_3CN$ may also be used as CO fumigants.

The pest control method according to the invention may be used for any purpose. For instance, rooms where the pests reside can be fumigated, e.g., storage areas, museums, churches, mills, cargo holds of ships, railroad cars, and silos. Individual goods to be fumigated can be placed into mobile tents. Mobile chambers, containers, even buildings, e.g., residential buildings, can be fumigated. It is of course useful to seal the corresponding rooms or containers, so that no fumigant can reach the environment. The containers or buildings can also be wrapped in foil in a known manner to prevent treatment gas from escaping into the atmosphere. A seal to prevent gas exchange, as described in the Internet under http://www.morse-associates.com/pressure.html, in the chapter entitled "Relative Pressure in Work Area," can also be ensured by adhesive tape, strippable coatings, or caulking. Both installed or uninstalled building timber can be treated. For instance, freshly cut or sawed timber can be placed into a tent, a fumigation chamber, or a foil envelope for fumigation. This can prevent the spreading of pests in export/import (quarantine fumigation).

Preferably, the method according to the invention is used for controlling the known storage pests and material pests (particularly wood pests), e.g., the tobacco beetle, the grain weevil, moths, flour mites, rice weevils, deathwatch beetles, woodworms, house longhorn beetle, or carpet beetles. The method can also be used to control termites.

The method according to the invention may also be used for soil fumigation. In this case, for instance nematodes and other vermin are destroyed.

Measures that are typically used in fumigation may be taken, e.g., working at an elevated temperature. It is advantageous if the temperature in pest control is at least 10° C., preferably between 15° and 35° C. The work is preferably done at a temperature that is at maximum 3° C. below the boiling point of the compound. Particularly preferred is fumigation at or above the boiling point. This is why carboxylic acid fluorides with their relatively low boiling point are particularly suitable for temperature-sensitive materials.

To achieve a high mortality rate of the storage, soil and wood pests as well as rodents, harmful insects or fungi to be controlled, the concentration preferably ranges from 0.1 $g/m^3$ to 200 $g/m^3$, and the duration is adjusted accordingly. The higher the concentration, the shorter is the contact time required.

The treatment gas can be delivered via water or alkaline solutions or alkali and is subsequently decomposed into harmless compounds. The gas may also be recovered through sorption, e.g., on a molecular sieve or activated carbon. Thermal decomposition or catalytic decomposition (incineration, pyrolysis, high-temperature hydrolysis) is also possible.

The invention also relates to mixtures of carboxylic acid fluorides and at least one other known pesticide. The preferred additional pesticides are the aforementioned agents. Mixtures of carboxylic acid fluorides and $CO_2$, in the form of a gas, liquid or solid, are particularly preferred. These mixtures may also contain additional pesticides.

The invention broadens the spectrum of useful fumigants, for which there is currently a desperate need, since MeBr has meanwhile been found to damage the ozone. Carboxylic acid fluorides act very quickly, which is of course advantageous in practice. After hydrolysis, acetyl fluoride forms acetic acid, which is found in nature.

Carboxylic acid fluorides can be produced, for example, from carboxylic acid chlorides and HF adducts of amines as described in co-pending U.S. patent application Ser. No. 09/856,909 (=WO 00/32549), the disclosure of which is incorporated herein by reference.

The following examples are intended to illustrate the invention in further detail, without limiting its scope.

EXAMPLES

General

Pests used:
a) Storage Pests
  a1) Mealworm beetle (*Tenebrio molitor*)=TENEMO
    Size: 12–18 mm, found all over Europe in grain, flour, and flour products. One of the worst pests in Germany.
  a2) Rice weevil (*Sitophilus oryzae*)=SITTOR
    Size: 2.3–3.5 mm. Found in the tropics, the subtropics, and in warm warehouses in Europe. Feeds on all types of grain and flour products. Feared storage pest in warm climates.
  a3) Broad-horned flour beetle (*Gnathocerus cornutus*)= GNATCO
    Size: 3.5–4 mm. Frequently found in mills, grain silos and bakeries. Beetles and larvae feed on grain and grain products.
  a4) Saw-toothed grain beetle (*Oryzaephilus surinamensis*)=ORYZSA
    Size: 2.5–3.5 mm. Common throughout the world, feeds on grain, flour, and grain products.
b) Wood Pests
  b1) House longhorn beetle (*Hylotrupes bajulus*)= HYLOBA
    Size: 7–21 mm. Feared pest; the larvae completely destroy old pine timber used in buildings. House longhorn infestations have recently increased significantly (due to the use of sapwood).
  b2) Common furniture beetle (*Anobium punctatum*)= NOBPU
    Size: 2.5–5 mm. Found in processed timber, old furniture, art treasures.
c) American drywood termites (*Cryptotermes brevis*)= CRYPBR, and *Incisitermes tabogae*=INCITA
    Size: 2.0–5 mm. These species are found primarily in the U.S. where they infest wooden houses and often cause severe damage if the houses are not promptly treated.

Fumigants:
  Trifluoroacetyl fluoride (TFAF),
  acetyl fluoride (ACF),
  chlorodifluoroacetyl fluoride (CFAF), and
  $SO_2F_2$ (SF) (for comparison).

Procedure

The test organisms, separated by species, were placed into a glass vessel measuring 30 cm×30 cm×60 cm, which was sealed with a glass lid so as to be airtight. The adults and the larvae of the mealworm beetle (*Tenebrio molitor*) and the broad-horned flour beetle (*Gnathocerus cornutus*) were placed into small glass vessels approximately 5 cm in diameter, which were closed with a gauze lid and in which they could freely move about. The larvae of the rice weevil had burrowed into seeds of grain. The wood pest larvae were inserted into small blocks of wood measuring 5 cm×2.5 cm×2 cm. The openings were sealed with wads of cotton wool. Only one each of the larvae of the house longhorn beetle (*Hylotrupes bajulus*) was inserted into a piece of wood, while 6–8 larvae of the common furniture beetle (*Anobium punctatum*) were inserted into each piece of wood.

The respective gas was then introduced into the fumigation vessel through a gas line from a gas tank that contained the specified amount of gas. After a defined time period, the fumigation vessel was purged with compressed air. The discharged gas was purified by an attached gas scrubber.

The beetles were observed until they died. This point was recorded for each species. The larvae of the wood pests as well as the larvae of the rice weevil (*Sitophilus oryzae*) had to be picked out of the wood or the grain to check their condition. If any of the animals were still alive, the wooden test blocks remaining in the vessel were fumigated again and were reexamined after the corresponding time span had elapsed. The same number of animals in the untreated control was also checked at each point.

The vitality of the animals was checked at certain time intervals. The beetles could be observed through the fumigation vessel. This was also true for the larvae of the mealworm beetle and the broad-horned flour beetle. The wooden test blocks of the wood pest larvae were opened with hammer and chisel. Tweezers were used to pull the rice weevil larvae out of the grain seeds. The exact time intervals and the number of the evaluated pests were documented in the test results.

Example 1

Use of Trifluoroacetyl Fluoride Against Wood Pests

|  | 1st Fumigation | 2nd Fumigation |
|---|---|---|
| Air temperature | 16° C. | 13° C. |
| Rel. air humidity | 66% | 66% |
| Gas amount/vessel | 2.74 g | 2.9 g |
| Gas concentration | 54.8 g/m$^3$ | 58.0 g/m$^3$ |

Result:

|  | Time after Start of Fumigation | | | | | | | |
|---|---|---|---|---|---|---|---|---|
|  | 1 hr. Number | | 3 hrs. Number | | 24 hrs. Number | | 48 hrs. Number | |
| Pests (Bayer) | dead | alive | dead | alive | dead | alive | dead | alive |
| HYLOBA | 4 | 2 | 6 | 0 | — | — | — | — |
| HYLOBA larvae | — | — | — | — | 0 | 6 | 3 | 3 |
| ANOBPU | 6 | 0 | — | — | — | — | — | — |
| ANOBPU larvae | — | — | — | — | 0 | 10 | 4 | 6 |

Exposed beetles and larvae were killed relatively quickly. After 1–2 minutes, the animals became very active. After about 10 minutes, all the beetles lay on their backs and only their legs and feelers were moving slightly. Larvae without wooden test blocks were dead after approximately 1 hour. The gas does not penetrate the wood sufficiently within a time span of 48 hours to kill the larvae completely. The beetles and larvae of the control were all still alive.

Example 2

Use of Trifluoroacetyl Fluoride Against Wood Pests, Air Circulation Through Ventilators

|  | 1st Fumigation | 2nd Fumigation |
|---|---|---|
| Air temperature | 20.6° C. | 21.5° C. |
| Rel. air humidity | 66% | 56% |
| Gas amount/vessel | 2.88 g | 2.40 g |
| Gas concentration | 57.6 g/m$^3$ | 48.0 g/m$^3$ |

Test with ventilator operation in the fumigation vessel

|  | Time after Start of Fumigation | | | | | | | |
|---|---|---|---|---|---|---|---|---|
|  | 1 hr. Number | | 12 hrs. Number | | 24 hrs. Number | | 48 hrs. Number | |
| Pests (Bayer) | dead | alive | dead | alive | dead | alive | dead | alive |
| HYLOBA | 5 | 1 | 6 | 0 | — | — | — | — |
| HYLOBA larvae | — | — | 0 | 7 | 0 | 7 | 1 | 6 |
| ANOBPU | 6 | 0 | — | — | — | — | — | — |
| ANOBPU larvae | — | — | 1 | 11 | 2 | 10 | 12 | 0 |

Even with ventilators, there was no improvement in the effectiveness with respect to the larvae.

Example 3

Use of Trifluoroacetyl Fluoride Against Storage Pests

|  | 1st Fumigation | 2nd Fumigation |
|---|---|---|
| Air temperature | 17.2° C. | 17.7° C. |
| Rel. air humidity | 54% | 54% |
| Gas amount/vessel | 2.29 g | 2.27 g |
| Gas concentration | 45.8 g/m$^3$ | 45.4 g/m$^3$ |

Result:

|  | Time after Start of Fumigation | | | | | | | |
|---|---|---|---|---|---|---|---|---|
|  | 1 hr. Number | | 3 hrs. Number | | 6 hrs. Number | | 12 hrs. Number | |
| Pests | dead | alive | dead | alive | dead | alive | dead | alive |
| TENEMO | 15 | 0 | — | — | — | — | — | — |
| TENEMO larvae | 15 | 0 | — | — | — | — | — | — |
| SITTOR | 20 | 0 | — | — | — | — | — | — |
| SITTOR larvae | 15 | 5 | 20 | 0 | — | — | — | — |
| GNATCO | 15 | 0 | — | — | — | — | — | — |
| GNATCO larvae | 15 | 0 | — | — | — | — | — | — |
| ORYZSA | 15 | 0 | — | — | — | — | — | — |

Example 4

Use of Acetyl Fluoride Against Storage Pests

| Air temperature: | 19.3° C. |
|---|---|
| Rel. air humidity: | 54% |
| Gas amount/vessel: | 1.82 g |
| Gas concentration: | 36.5 g/m$^3$ |

Result:

|  | Time after Start of Fumigation | | | | | | | |
|---|---|---|---|---|---|---|---|---|
|  | 1 hr. Number | | 2 hrs. Number | | 12 hrs. Number | | 24 hrs. Number | |
| Pests | dead | alive | dead | alive | dead | alive | dead | alive |
| TENEMO | 10 | 0 | — | — | — | — | — | — |
| TENEMO larvae | 5 | 5 | 10 | 0 | — | — | — | — |
| SITTOR | 25 | 0 | — | — | — | — | — | — |
| SITTOR larvae | — | — | — | — | — | — | 25 | 0 |
| GNATCO | 12 | 13 | 22 | 3 | 25 | 0 | — | — |
| GNATCO larvae | 25 | 0 | — | — | — | — | — | — |
| ORYZSA | 25 | 0 | — | — | — | — | — | — |

In addition to the storage pests, 3 house longhorn beetles and larvae as well as 2 common furniture beetle larvae were tested. The house longhorn beetles were dead after 15 minutes.
After 24 hours, the larvae of the wood pests were dead. An earlier effect, if any, was not determined because evaluation only took place after 24 hours.

Example 5

Comparison of Action of Acetyl Fluoride (ACF) and Sulfuryl Fluoride (SF) on Wood and Storage Pests

|  | 1st Fumigation | 2nd Fumigation | 3rd Fumigation |
|---|---|---|---|
| Air temperature | 23° C. | 23° C. | 22° C. |
| Rel. air humidity | 55% | 55% | 54% |
| Gas amount/vessel ACF | 2.53 g | 2.41 g | 2.57 g |
| Gas amount/vessel SF | 2.37 g | 2.33 g | 2.05 g |
| Gas concentration ACF | 50.6 g/m$^3$ | 48.2 g/m$^3$ | 51.4 g/m$^3$ |
| Gas concentration SF | 47.4 g/m$^3$ | 44.6 g/m$^3$ | 41 g/m$^3$ |

Result:

|  |  | Time after Start of Fumigation | | | | | | | |
|---|---|---|---|---|---|---|---|---|---|
|  |  | 30 min. Number dead/alive | | 1 hr. Number dead/alive | | 3 hrs. Number dead/alive | | 6 hrs Number dead/alive | |
| Test Agent | Pest | | | | | | | | |
| ACF | HYLOBA | 4 | 0 | — | — | — | — | — | — |
| SF | HYLOBA | 0 | 4 | 2 | 2 | 4 | 0 | — | — |
| ACF | HYLOBA larvae | — | — | 4 | 0 | 2 | 1 | 7 | 0 |
| SF | HYLOBA larvae | — | — | 1 | 3 | 4 | 0 | 6 | 0 |
| ACF | ANOBPU | 6 | 0 | — | — | — | — | — | — |
| SF | ANOBPU | 6 | 0 | — | — | — | — | — | — |
| ACF | ANOBPU larvae | — | — | 3 | 1 | 2 | 2 | 8 | 0 |
| SF | ANOBPU larvae | — | — | 0 | 3 | 0 | 4 | 8 | 0 |
| ACF | TENEMO | 10 | 0 | — | — | — | — | — | — |
| SF | TENEMO | 10 | 0 | — | — | — | — | — | — |
| ACF | TENEMO larvae | 10 | 0 | — | — | — | — | — | — |
| SF | TENEOMO larvae | 4 | 1 | 4 | 1 | 5 | 0 | — | — |
| ACF | SITTOR | 15 | 0 | — | — | — | — | — | — |
| SF | SITTOR | 15 | 0 | — | — | — | — | — | — |
| ACF | SITTOR larvae | — | — | 15 | 0 | — | — | — | — |
| SF | SITTOR larvae | — | — | 15 | 0 | — | — | — | — |
| ACF | GNATCO | 15 | 0 | — | — | — | — | — | — |
| SF | GNATCO | 15 | 0 | — | — | — | — | — | — |
| ACF | GNATCO larvae | 15 | 0 | — | — | — | — | — | — |
| SF | GNATCO larvae | 0 | 15 | 15 | 0 | — | — | — | — |
| ACF | ORYZSA | 15 | 0 | — | — | — | — | — | — |
| SF | ORYZSA | 15 | 0 | — | — | — | — | — | — |

Sulfuryl fluoride clearly acts more slowly than acetyl fluoride.
Conclusion: Both acetyl fluoride and trifluoroacetyl fluoride are very effective against exposed beetles and larvae. Acetyl fluoride is very effective against wood pests, especially at temperatures in excess of 20° C. (i.e., near or above the boiling point). It decomposes to harmless acetic acid with ventilation or can be converted to harmless acetates with bases.

Example 6

Termite Control

Acetyl fluoride was used to control termites. A comparison test showed it to be as effective as $SO_2F_2$. It was particularly effective against *Cryptotermes*.

|  | 1st Fumigation | 2nd Fumigation | 3rd Fumigation |
|---|---|---|---|
| Air temperature | 23.7° C. | 24° C. | — |
| Rel. air humidity | 51% | 66% | — |
| Gas amount/vessel ACF | 2.50 g | 2.69 g | — |
| Gas amount/vessel SF | 2.39 g | 2.24 g | — |
| Gas concentration ACF | 50.0 g/m$^3$ | 53.8 g/m$^3$ | — |
| Gas concentration SF | 47.8 g/m$^3$ | 44.8 g/m$^3$ | — |

Result:

|  |  | Time after 1st Fumigation | | | | | |
|---|---|---|---|---|---|---|---|
|  |  | 30 min. Number dead/alive | | 1 hr. Number dead/alive | | 3 hrs. Number dead/alive | |
| Test Agent | Pest | | | | | | |
| ACF | CRYPBR | 0 | 180 | 0 | 60 | 120 | 0 |
| SF | CRYPBBR | 0 | 180 | 0 | 60 | 120 | 0 |
| ACF | INCITA | 0 | 90 | 0 | 30 | 60 | 0 |
| SF | INCITA | 0 | 90 | 0 | 30 | 60 | 0 |

ACF = acetyl fluoride
SF = sulfuryl fluoride

Although all fumigated termites were still alive after 1 hour, they were weakened and less lively than those of the control. The termites treated with sulfuryl fluoride were more lively overall after 1 hour of fumigation than those treated with acetyl fluoride. After a 24-hour observation period, these animals were reexamined. All of the *Crypto-*

*termes* treated with acetyl fluoride were dead. Only 3 out of 30 of the *Incisitermes* were still alive. All *Incisitermes* treated with sulfuryl fluoride were dead and 7 out of 60 of the *Cryptotermes* were still alive. After 3 hours of fumigation, all animals were dead.

Overall, it can be stated that acetyl fluoride can penetrate wood more quickly, and a slightly faster effect is achieved as a result. This became clear based on the termites examined within the described time intervals. The animals fumigated with sulfuryl fluoride were somewhat livelier than those treated with acetyl fluoride.

Example 7

Parallel Test—Acetyl Fluoride/Chlorodifluoroacetyl Fluoride for Wood and Storage Pests

|  | 1st Fumigation | 2nd Fumigation | 3rd Fumigation |
|---|---|---|---|
| Air temperature | 20.0° C. | 20.2° C. | 19.8 C. |
| Rel. air humidity | 70% | 65% | 60% |
| Gas amount/vessel ACF | 2.65 g | 2.73 g | 0 |
| Gas amount/vessel SF | 2.18 g | 2.07 g | 1.99 g |
| Gas concentration ACF | 53.0 g/m$^3$ | 54.6 g/m$^3$ | 0 |
| Gas concentration SF | 43.6 g/m$^3$ | 41.4 g/m$^3$ | 39.8 g/m$^3$ |

| Test Agent | Pest | 30 min. Number dead/alive | | 1 hr. Number dead/alive | | 3 hrs. Number dead/alive | | 6 hrs Number dead/alive | |
|---|---|---|---|---|---|---|---|---|---|
| ACF | HYLOBA | 3 | 3 | 6 | 0 | — | — | — | — |
| CFACF | HYLOBA | 6 | 0 | — | — | — | — | — | — |
| ACF | HYLOBA larvae | — | — | 3 | 2 | 10 | 0 | — | — |
| CFACF | HYLOBA larvae | — | — | 0 | 5 | 0 | 5 | 0 | 5 |
| ACF | ANOBPU larvae | — | — | 1 | 5 | 4 | 2 | 2 | 4 |
| CFACF | ANOBPU larvae | — | — | 0 | 6 | 3 | 3 | 2 | 4 |
| ACF | TENEMO | 10 | 0 | — | — | — | — | — | — |
| CFACF | TENEMO | 0 | 10 | 0 | 10 | 0 | 10 | 5 | 5 |
| ACF | TENEMO larvae | 5 | 5 | 10 | 0 | — | — | — | — |
| CFACF | TENEMO larvae | 0 | 10 | 0 | 10 | 10 | 0 | — | — |
| ACF | SITTOR | 15 | 0 | — | — | — | — | — | — |
| CFACF | SITTOR | 8 | 7 | 8 | 7 | 15 | 0 | — | — |
| ACF | GNATCO | 15 | 0 | — | — | — | — | — | — |
| CFACF | GNATCO | 15 | 0 | — | — | — | — | — | — |
| ACF | GNATCO larvae | 15 | 0 | — | — | — | — | — | — |
| CFACF | GNATCO larvae | 8 | 7 | 8 | 7 | 15 | 0 | — | — |
| ACF | ORYZSA | 15 | 0 | — | — | — | — | — | — |
| CFACF | ORYZSA | 15 | 0 | — | — | — | — | — | — |

ACF = acetyl fluoride
CFACF = chlorodifluoroacetyl fluoride

It is apparent that acetyl fluoride is superior to chlorodifluoroacetyl fluoride against several of the pest species tested.

The foregoing description and examples have been set forth merely to illustrate the invention and are not intended to be limiting. Since modifications of the described embodiments incorporating the spirit and substance of the invention may occur to persons skilled in the art, the invention should be broadly construed to include all variations falling within the scope of the appended claims and equivalents thereof.

What is claimed is:

1. A method of destroying pests by fumigation comprising subjecting said pests to an effective pesticidal amount in the range of 0.1 g/m$^3$ to 200 g/m$^3$ of a carboxylic acid fluoride having at least 2 carbon atoms and having a boiling point of less than 100° C. for a time sufficient to kill said pests.

2. A method according to claim 1, wherein said carboxylic acid fluoride has a boiling point of less than 45° C.

3. A method according to claim 2, wherein said carboxylic acid fluoride has a boiling point of less than 30° C.

4. A method according to claim 1, wherein said carboxylic acid fluoride corresponds to the formula RC(O)F, where R represents $CH_3$, $C_2H_5$, $CF_3$, $CF_2H$ or $CF_2Cl$.

5. A method according to claim 1, wherein said carboxylic acid fluoride is used in admixture with at least one additional pesticide.

6. A method according to claim 1, wherein said carboxylic acid fluoride is used in admixture with a substance selected from the group consisting of sulfuryl fluoride, sulfuryl chlorofluoride, nitrogen, noble gases, $CO_2$, carbonyl sulfide, $PH_3$, alkyl phosphines, $SF_6$, inorganic or organic compounds with the CN group, organic esters, organic nitro compounds, halogenated hydrocarbons, alkynols, thiocyante esters, isothiocyanate esters, chloropicrin, ethylene oxide, sulfonyl fluorides and atomizing agents.

7. A method according to claim 5, wherein said at least one additional pesticide comprises carbon dioxide.

8. A method of destroying pests by fumigation comprising subjecting said pests to an effective pesticidal amount in the range of 0.1 g/m$^3$ to 200 g/m$^3$ of a carboxylic acid fluoride having at least 3 carbon atoms or having at least 2 carbon atoms and at least 2 halogen atoms for a time sufficient to kill said pests, said carboxylic acid fluoride having a boiling point of less than 100° C.

9. A method according to claim 8, wherein said carboxylic acid fluoride has a boiling point of less than 45° C.

10. A method according to claim 9, wherein said carboxylic acid fluoride has a boiling point of less than 30° C.

11. A method according to claim 8, wherein said carboxylic acid fluoride corresponds to the formula RC(O)F, where R is $C_2H_5CF_3$, $CF_2H$, or $CF_2Cl$.

12. A method according to claim 8, wherein said carboxylic acid fluoride is used in admixture with at least one additional pesticide.

13. A method according to claim 8, wherein said carboxylic acid fluoride is used in admixture with a substance selected from the group consisting of sulfuryl fluoride, sulfuryl chlorofluoride, nitrogen, noble gases, $CO_2$, carbonyl sulfide, $PH_3$, alkyl phosphines, $SF_6$, inorganic or organic compounds with the CN group, organic esters, organic nitro compounds, halogenated hydrocarbons, alkynols, thiocyanate esters, isothiocyanate esters, chloropicrin, ethylene oxide, sulfonyl fluorides and atomizing agents.

14. A method according to claim 12, wherein said at least one additional pesticide comprises carbon dioxide.

15. A method according to claim 8, wherein said carboxylic acid fluoride corresponds to the formula RC(O)F, where R is $C_2H_5$, $CF_2H$, or $CF_2Cl$.

* * * * *